United States Patent [19]

Pomeranz

[11] Patent Number: 4,564,006
[45] Date of Patent: * Jan. 14, 1986

[54] RECLOSABLE CONDOM

[76] Inventor: Mark L. Pomeranz, 9760 Viceroy Dr. East, Jacksonville, Fla. 32217

[*] Notice: The portion of the term of this patent subsequent to Feb. 12, 2002 has been disclaimed.

[21] Appl. No.: 634,442

[22] Filed: Jul. 25, 1984

Related U.S. Application Data

[63] Continuation of Ser. No. 490,450, May 2, 1983, Pat. No. 4,498,466, which is a continuation-in-part of Ser. No. 388,107, Jun. 15, 1982, Pat. No. 4,432,357.

[51] Int. Cl.⁴ .............................................. A61F 5/00
[52] U.S. Cl. ..................................... 128/79; 604/347; 604/349
[58] Field of Search ................ 604/346, 347, 349–353, 604/327, 330, 335; 128/132 R, 157, 132, 79; 383/66; 24/201 C, 563, 580

[56] References Cited

U.S. PATENT DOCUMENTS

| | | | |
|---|---|---|---|
| 1,216,099 | 2/1917 | Falck | 128/79 |
| 2,358,653 | 9/1944 | Mock | 150/6 |
| 2,442,044 | 5/1948 | Howard | 24/384 |
| 2,454,214 | 11/1948 | Sapp | 24/384 |
| 2,471,360 | 5/1949 | Thorne | 128/79 |
| 2,586,674 | 2/1952 | Lonne | |
| 2,756,172 | 7/1956 | Kidd | 24/201 C |
| 2,904,041 | 9/1959 | Brown | 128/132 R |
| 3,788,324 | 1/1974 | Lim | 604/352 |
| 4,224,933 | 9/1980 | Reiling | 128/79 |
| 4,353,360 | 10/1982 | Finney et al. | 128/79 |
| 4,378,792 | 4/1983 | Finney | 128/79 |
| 4,498,466 | 2/1985 | Pomeranz | 604/347 |

FOREIGN PATENT DOCUMENTS

| | | | |
|---|---|---|---|
| 355426 | 10/1905 | France | 604/349 |
| 7502231 | 8/1976 | Netherlands | 383/63 |
| 8641 | of 1900 | United Kingdom | 604/349 |

OTHER PUBLICATIONS

Appearance of Myelin Forms in Rheopexic Dispersion of Dioctyl Sodium Sulfosuccinate, Levinson et al., Journal of Pharmaceutical Sciences, vol. 65, No. 8, Aug. 1976, pp. 1265–1266.

Rheological Characterization of Dioctyl Sodium Sulfosuccinate in Normal Saline and Distilled Water, Journal of Colloid and Interface Science, vol. 56, No. 2, Aug., 1976, pp. 388–390.

Effect on pH on Rheopexic Dispersion of Dioctyl Sodium Sulfo–Sulfosuccinate Dispersal in Normal Saline, Levinson et al, Journal of Colloid and Interface Science, vol. 72, No. 1, Oct. 15, 1979, pp. 159–160.

*Primary Examiner*—Stephen C. Pellegrino
*Assistant Examiner*—J. L. Kruter
*Attorney, Agent, or Firm*—Frishauf, Holtz, Goodman & Woodward

[57] ABSTRACT

A condom comprises an elongated generally tubular member of thin, flexible material and having an elongated opening provided along at least a substantial portion of the length of the elongated tubular member so as to facilitate placing the elongated tubular member over a flaccid penis. The elongated tubular member may contain a plurality of compartments, each of which contains rheopexic material so that the condom stiffens in use. A slide fastener closure device is provided for closing the elongated opening after placing the condom on a flaccid penis. Further disclosed is an elongated generally tubular member containing rheopexic material for use as an implanted penile prosthesis which stiffens upon agitation.

14 Claims, 13 Drawing Figures

RECLOSABLE CONDOM

CROSS REFERENCE TO RELATED APPLICATION

This is a continuation of application Ser. No. 490,450, filed May 2, 1983 now U.S. Pat. No. 4,498,466, issued Feb. 12, 1985 which is a continuation-in-part of Ser. No. 388,107, filed June 15, 1982 now U.S. Pat. No. 4,432,357, issued Feb. 21, 1984.

BACKGROUND OF THE INVENTION

This invention relates to condom, and more particularly to a condom which may be easily affixed even to a flaccid penis, and also to implant-type stiffening devices.

At present, two types of condoms are known: the roll on type which rolls over the penis; and the pull over type which is pulled over the penis. Both of these known condoms are suitable for use only when the penis is erect. If the penis is flaccid, for example as would be the case with an impotent male, it is extremely difficult, if not impossible to place the condom on the penis.

More particularly, when condoms using rheopexic fluid as a stiffening agent, as disclosed and claimed in my copending U.S. patent application Ser. No. 388,107, which condoms are particularly suitable for use with impotent males, it is difficult to place the condom over the flaccid penis.

Therefore, an object of the present invention is to provide a condom which may be easily placed over the penis of the user, even a flaccid penis of an impotent male.

Penile implants are presently well known. Typical penile implants are discussed in an article entitled, "Complications of Penile Prosthesis Surgery for Impotence" by Joseph J. Kaufman, Arie Lindner and Shlomo Raz, The Journal of Urology, Volume 128, December, 1982, pages 1192 and 1193, the entire contents of which are incorporated herein by reference. Penile prosthetic devices are also discussed in the article entitled, "Penile Prosthetic Surgery Under Local Anesthesia" by Joseph J. Kaufman, The Journal of Urology, Volume 128, December, 1982, pages 1190 and 1191, the entire contents of which are also incorporated herein by reference. The known penile prosthesis is generally a semi-rigid rod or an inflatable device. The semi-rigid rod has the disadvantage of always being semi-rigid. The inflatable device has the disadvantage of requiring additional structures to inflate and deflate the prosthesis. These prior art devices are thus unsatisfactory.

Therefore, a further object of the present invention is to provide a penile prosthesis which may be easily implanted in the penis and which is simpler in design and operation than the prior art devices.

Yet another object of the invention is to provide a condom which may be easily placed over the penis of the user, even a flaccid penis of an impotent male, which condom need not include the stiffening rheopexic material disclosed herein and disclosed in my copending application Ser. No. 388,107. Such a condom is particularly useful with impotent males using other penis stiffening means, and who require the use of a condom for birth and/or disease control.

SUMMARY OF THE INVENTION

According to the present invention, a condom comprises an elongated generally tubular member of thin, flexible material; an elongated opening provided along at least a substantial portion of the length of the elongated tubular member so as to facilitate placing the elongated tubular member over a flaccid penis; and means for closing the elongated opening after placing of the condom on a flaccid penis. Preferably, the tubular member has chambers thereon for receiving rheopexic material to serve as a stiffening agent.

A penile prosthesis according to the present invention comprises an elongated generally tubular member having closed ends and defining at least one chamber therein; and a rheopexic material in the at least one chamber and retained sealingly within the at least one chamber; the elongated tubular member being adapted to be implanted in a penis.

DETAILED DESCRIPTION

The condoms of the present invention preferably are generally of the type illustrated in U.S. patent application Ser. No. 388,107. The condom is provided with a plurality of chambers or compartments 10 illustrated in FIG. 2, which compartments are filled with rheopexic fluid of the type disclosed in Ser. No. 388,107, the rheopexic fluid not being discussed in detail herein. Also, the various compartments containing the rheopexic fluids may be of the type shown in Ser. No. 388,107, a detailed description not being given herein since the entire contents of Ser. No. 388,107 is incorporated herein by reference. The compartments are shown schematically in FIGS. 2 and 3, but are not shown in the other drawings of the present application.

While the present invention is particularly useful with condoms using rheopexic fluid therein as a stiffening agent, the concepts of the present invention can be used with other types of condoms having other stiffening devices and wherein the penis may be provided with an internal implant-type stiffening device. The concepts of the present invention are also applicable to condoms having no stiffening means per se or to condoms having stiffening means other than those specifically disclosed herein. The main object of the present invention is to provide a condom which can be placed on a flaccid penis, for example by impotent males.

Figure 1:
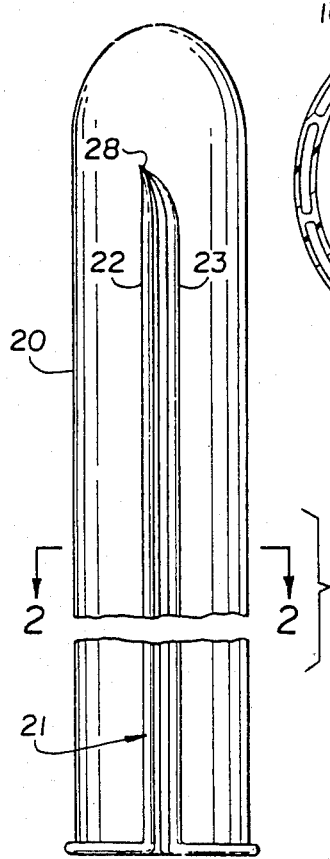
FIG. 1 is a perspective view of a condom, in its erected state, according to the present invention.
Figure 2:
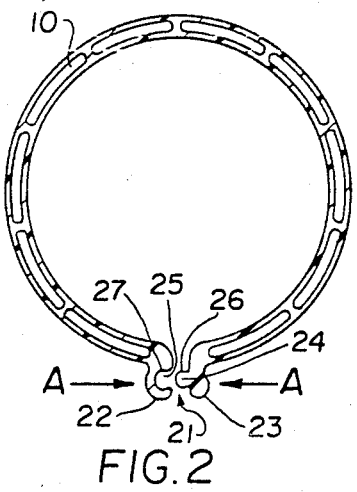
FIG. 2 is a cross-sectional view of the condom of FIG. 1, drawn to an enlarged scale.

Referring to FIG. 1, the condom 20 comprises, for example, a condom as shown in Ser. No. 388,107 with inner and outer layers, having rheopexic fluid therein. The condom is further provided with an elongated opening member 21 which may be generally of the type designated as a "zip-lock" closure. The closure is shown in more detail in FIG. 2. The closure 21 comprises interengaging members 22, 23, the member 23 having a projection 24 thereon which engages in a recess 25 of member 22. Preferably, the projection 24 has a protrusion 26 which engages in a concave portion 27 of the recess 25 to provide a firm interlocking engagement of the projection 24 in the recess 25. The closure in FIGS. 1 and 2 is closed by pressing the members 22, 23 together along the direction of the arrows A shown in FIG. 2. This will provide a firm, liquid-tight seal along the length of the condom, and since the condom is supplied with the locking members 22, 23 opened, the condom may be easily placed over the penis, the closure members 22, 23 then being pressed together in the direction of the arrows A in FIG. 2, to firmly close the condom over the penis, ready for use. Preferably, the locking members 22, 23 are fabricated of a material which is firmer than that of the material forming the circular part of the condom. Also, the condom preferably has about one inch at the top thereof which is solid or closed (not provided with the zip-type opening) for accumulation of ejaculated spermatozoa. By providing the solid or closed upper or head portion of the condom, the safety aspect of preventing possible leakage of spermatozoa after ejaculation is improved.

Figure 3:
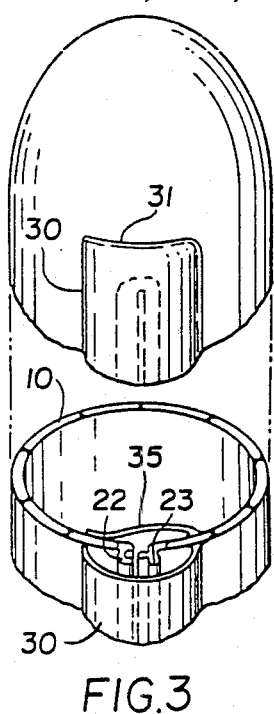
FIG. 3 is a partial perspective, partial cross-sectional view of a modified condom of FIG. 1, but provided with a protective flap, drawn to an enlarged scale.

As shown in FIG. 3, a flap, of latex or having compartments containing rheopexic fluid, can be provided to go over the zip-type closure of FIGS. 1 and 2 to prevent irritation from occurring to the sex partner. Preferably, the flap 30 illustrated in FIG. 3 extends upwardly above the upper portion of closure member 22, 23 and is adhered or sealed to the condom at 31. This insures that the flap will remain covering the closure members 22, 23 during use, and provides a smoother outer surface of the condom to further prevent irritation from occurring to the sex partner.

As shown in FIG. 3 an inner flap 35 may be provided to protect the male organ from irritation due to the closure 22, 23. The inner flap 35 is preferably generally coextensive with outer flap 30.

Figure 4:
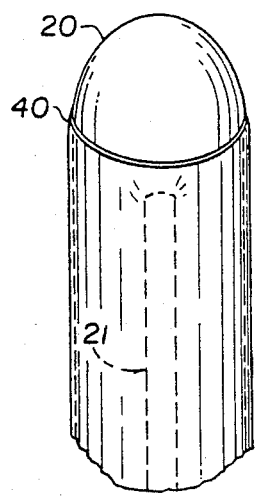
FIG. 4 is a further example of the invention wherein the protective flap of FIG. 3 is replaced with a protective sleeve.

FIG. 4 illustrates a modified protective arrangement wherein a sleeve 40 is slid over the condom after the condom is placed over the penis. For example, after the condom is placed over the penis and the zip-closure members 22, 23 are pressed together to close same, the sleeve 40 is then slipped over the closed condom to serve as a protection layer to prevent irritation to the sex partner.

Figure 5:
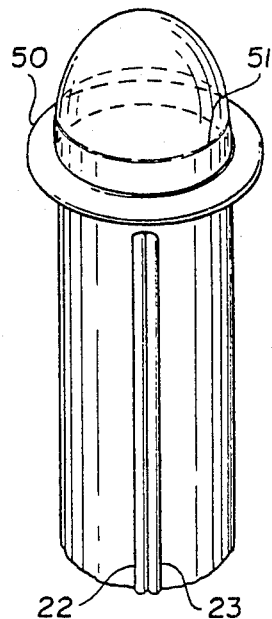
FIG. 5 illustrates a modification of the embodiment of FIG. 4 wherein the sleeve comprises a roll-down sleeve integrally formed with the front portion of the condom.
Figure 6:
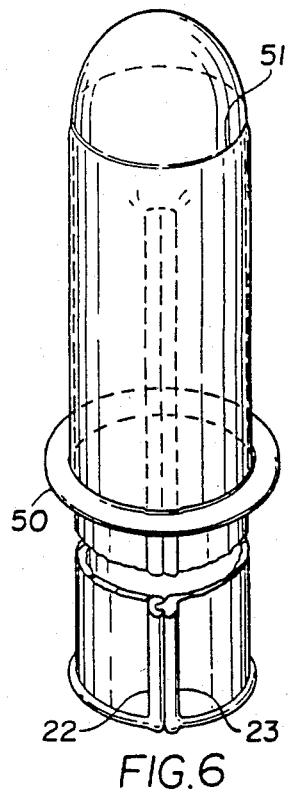
FIG. 6 illustrates the embodiment of FIG. 5 with the roll-down sleeve partially rolled down.

FIG. 5 illustrates an improved arrangement of providing a circular sleeve over the condom for protective purposes. In FIG. 5, the sleeve 50 is integrally formed at the upper portion 51 of the condom with the outer surface of the condom so as to provide a smooth junction which will not irritate the sex partner. The sleeve 50 is rolled up, as shown in FIG. 5. After closure of the zip closure members 22, 23, the sleeve 50 is then rolled downwardly to completely cover the zip closure member in a secure and positive fashion. FIG. 6 illustrates the roll-down sleeve 50 at an intermediate position, it being clear that sufficient material is provided in the roll-down sleeve 50 to permit it to be rolled all the way down to the base of the condom.

In the above embodiments, it should be clear that the zip-closure members 22, 23 are tapered at the upper ends or at the head portion of the condom, as shown in FIG. 1, to further prevent irritation to the sex partner. This is shown by means of inclined surfaces 28 in FIG. 1.

Figure 7:
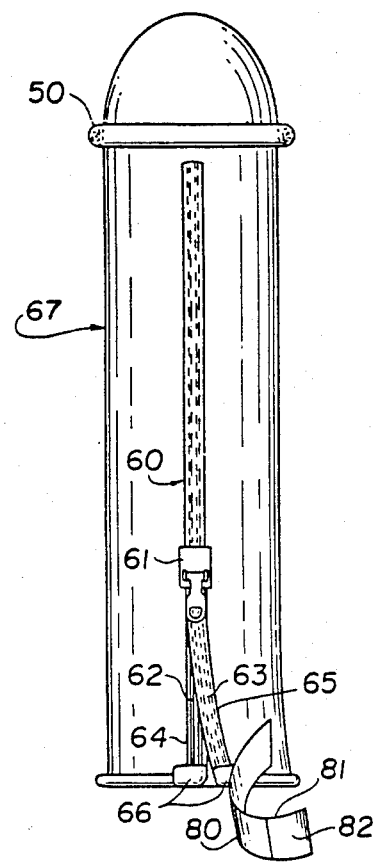
FIG. 7 illustrates a condom with a zip-type closure having a slide fastener device thereon.
Figure 8:
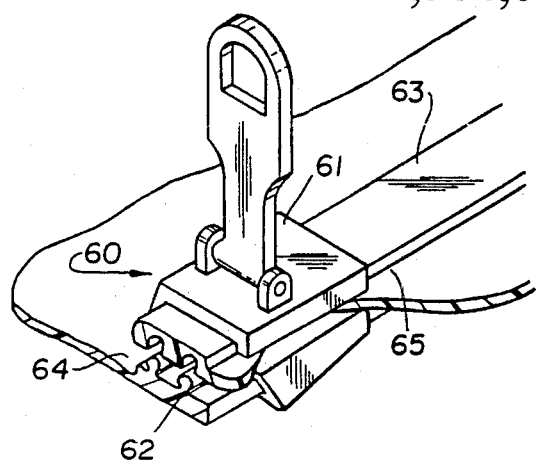
FIG. 8 is a detail perspective cross-section of one type of conventional slide fastener device as used in FIGS. 7, 9 and 10.

FIG. 7 illustrates a modified embodiment wherein the closure comprises a plastic slide fastener device 60 utilizing a conventional slide 61 for closing the plastic slide fastener. The plastic slide fastener members 62, 63 are integrally formed with edges 64, 65 of the condom, as are the closure members 22, 23 with the edges of the condom 20 shown in FIG. 1. The slide fastener 60 is of convention construction and is shown in detail in FIG. 8. To use the condom of FIG. 7, the condom, in its open state, is placed over the flaccid penis, and the slide 61 is pulled downwardly toward the base of the penis to firmly close the plastic slide fastener 60. The slide 61 can be removed completely from the condom at the base portion of the condom, or a stop member 66 can be formed at the bottom of the condom to prevent the slide 61 from coming off the base of the condom. This arrangement will permit the slide fastener 60 to be re-used, thereby permitting the condom to be re-used, as desired. If the stop members 66 are provided to prevent the slide 61 from coming off the end of the members 62,63, it is desirable that some type of protective device be provided at the base of the condom to prevent the retained slide 61 from irritating the sex partner. A suitable device is a sleeve such as shown in FIG. 4, but the sleeve not being as long as the sleeve of FIG. 4 since it is only necessary to cover the lower end portion of the slide fastener 60. Also, in this embodiment, it is preferable to use a flap such as flap 30 to protect the sex partner from irritation by the slide fastener 60. Sleeve 40 of FIG. 4 could also be used for protective purposes. The roll-down sleeve 50 of FIGS. 5 and 6 could also be used, this arrangement being very advantageous since it will also "roll" relatively easily over the slide 61 at the base portion of the condom to serve as a protector shield therefor.

As seen in FIG. 7, a flap 80 can be integrally formed with the lower portion of the condom 67, the flap 80 having an adhesive portion 81 covered by a release material (such as a release paper) 82. In use, when the 61 is zipped down to the bottom of the condom, the relase paper 82 is removed and the flap 80 is placed across the bottom portion of the condom, over the slide 61, and adhered to the opposite side of the condom, thereby covering the slide 61 and also securely locking the condom in its closed position to prevent inadvertent opening thereof. Such a flap 80 can also be provided in the embodiment of FIGS. 1 and 6 to insure that the bottom portion of the condom will remain closed. The flap 80 in the embodiment of FIGS. 1 and 6 is not illustrated in the drawings, but it can be implemented in substantially the same way as shown in FIG. 7. The inner and outer flaps 35, 30, respectively, shown in FIG. 3 may have adhesive portions along their longitudinal vertically extending free edges, the adhesive material being covered by a release paper or the like. During use, the free ends of the flaps 30 and/or 35 can be adhered to the remaining portion of the condom, if desired. It is generally not necessary to provide an adhesive for the inner flap 35 since it will be retained in place by the pressure of the condom on the penis. If adhesive securing of the free edge of a flap is desired, it is generally preferable to use it in connection with outer flap 30.

Figure 9:
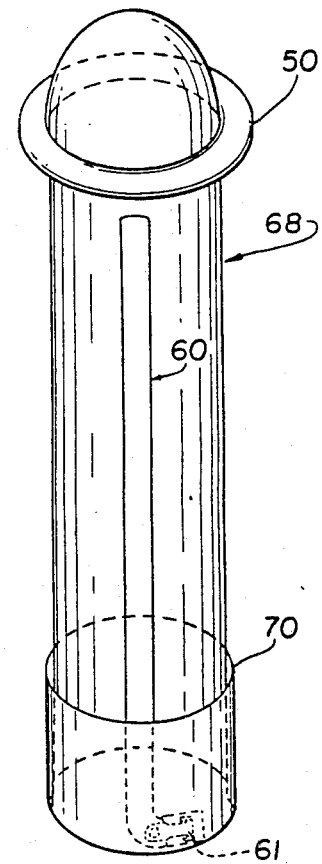
FIG. 9 illustrates a modified embodiment of FIG. 1 wherein the slide fastener device extends at a right angle to the longitudinal direction of the condom at the base or bottom portion thereof.
Figure 10:
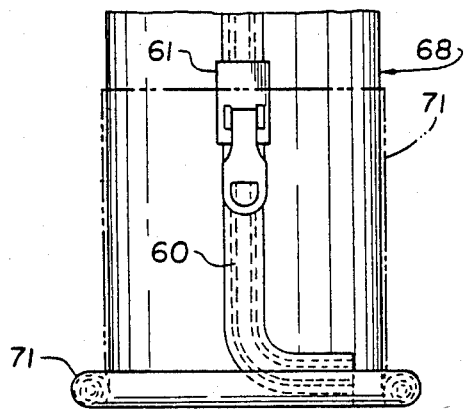
FIG. 10 illustrates a modification of the embodiment of FIG. 9.

FIG. 9 illustrates a further modified embodiment wherein the slide fastener 60 is turned at right angles at the base portion of the condom so that after the slide 61 is pulled down, the slide is retained in a horizontal, rather than vertical position relative to the penis. A protective sleeve 70 is provided at the base portion of the condom to serve as protection from irritation of the partner by the slide 61. The sleeve 70 is shown outwardly spaced from condom 68 in FIG. 9 for ease of illustration, but preferably it is of elastic material and is tightly formed against the main body of the condom 68. In the embodiment of FIG. 9, the roll-down sleeve 50 of FIGS. 5 and 6, is used. Alternatively, the slip-on sleeve 40 of FIG. 4 or the flap 30 of FIG. 3 can be provided either with or without the upwardly directed lower sleeve 70, for protective purposes. Still further, as seen in FIG. 10, the sleeve 70 can be provided in a roll-up manner, such as the roll-down sleeve 50 of FIGS. 5 and 6. In FIG. 9, after the slide 61 is slid down to the base of the condom 68, the roll-up sleeve 71 is rolled upwardly, as shown in chain lines, to cover the slide 61. The sleeve 71 is of elastic material and preferably tightly encircles the base of the condom so as to securely cover the slide 61.

In the embodiments of FIGS. 9 and 10, since a fixed member is located at the base of the condom, it is more difficult to insert the condom onto a flaccid penis than the embodiments discussed previously. However, if the slide fastener device for the elongated opening of the condom is in the open state during insertion of the penis, it is still possible to relatively easily insert the condom over the penis since the user can extend his fingers through the elongated open closure and pull the flaccid penis through the lower members 70 or 71 (FIGS. 9 and 10, respectively). After the penis is pulled through the lower portion 70, 71, then the condom can be closed in the longitudinal direction, as discussed hereinabove.

Once the condom of the present invention is placed on the penis, a "pseudo erection" can take place by means of the rheopexic material such as disclosed in Ser. No. 388,107, or by other means which may be provided either within the condom or within the penis of the user.

Any of the condoms of FIGS. 1-10 may be rheopexic fluid receiving chambers (as seen in FIG. 2) or such chambers may be eliminated. When the chambers are eliminated, the condom may be a single layer condom having the same opening and closing constructions as shown in FIGS. 1 and 3-10 to aid in placing the condom over a flaccid or semi-flaccid penis. Such a condom may have stiffening means other than rheopexic fluid or may have no stiffening means at all. Penile implants, such as those already known or those shown in FIGS. 11-13 may be used with such condoms which have rheopexic fluid receiving chambers as shown in FIG. 2.

Figure 11:
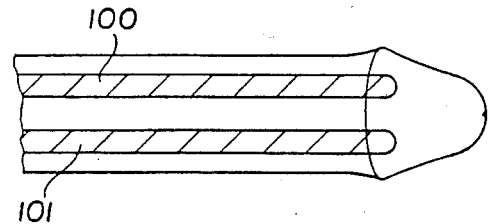
FIG. 11 illustrates the invention as applied to a penile prosthesis.
Figure 12:
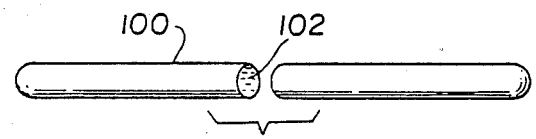
FIG. 12 illustrates a penile prosthesis of FIG. 11 in greater detail.

FIG. 11 shows a penile prosthesis which is implanted in a penis. FIG. 11 shows two penile prostheses 100, 101, which prostheses are generally elongated tubular members having rheopexic material therein. FIG. 12 shows a broken view of a typical prosthesis 100 with rheopexic fluid 102 therein. The advantage of the penile prosthesis of FIGS. 11 and 12 is that in the normal state, the tubular prosthesis 100 is generally flaccid. In an agitated state, the rheopexic material within the prosthesis 100, 101 will stiffen the prosthesis 100, 101 due to the characteristic of rheopexic materials, thereby providing a "psuedo erection". Upon cessation of stimulation, the rheopexic material will revert back to its normal, non-agitated state and the penis will then again become flaccid. These are precisely the characteristics required of a penile prosthesis.

The details of implanting a penile prosthesis of the present invention into a penis is not given herein since such details are known, as is evident from the two articles entitled "Complications of Penile Prosthesis Surgery for Impotence" and "Penile Prosthetic Surgery Under Local Anesthesia", which were mentioned hereinabove. The tubular members 100, 101 can be made of inert, flexible biologically safe materials, such as polypropylene or similar materials so as to contain the rheopexic material in a leak-proof or liquid-tight state. Similar materials as are used for inflatable penile prostheses can be used for the elongated tubular members 100, 101 of the present invention.

Figure 13:
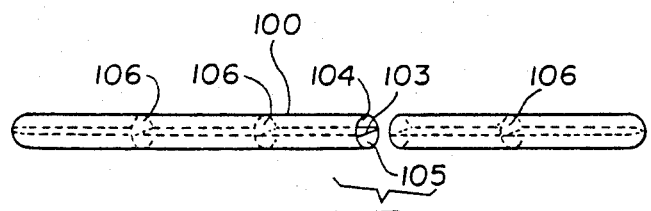
FIG. 13 illustrates a modified embodiment of the prosthesis of FIGS. 11 and 12.

The elongated prosthesis shown in FIGS. 11 and 12 can be provided with compartments or chambers therein, such as shown in FIG. 13. For example, a longitudinally extending divider 103 can be provided internally of the prosthesis 100 to divide same into upper and lower compartments 104, 105, each of which is sealed off from each other and each of which is filled with rheopexic material 102. The prosthesis of FIG. 13 can also be divided into adjacent longitudinally extending compartments by providing internal dividers 106 which extend vertically in FIG. 13. The longitudinal divider 103 and/or the vertically extending dividers 106 can be provided, as desired, depending upon the characteristics required and the type of rheopexic material used.

I claim:

1. A condom comprising:
   an elongated generally tubular member of thin, flexible material;
   an elongated opening provided along at least a substantial portion of the length of said elongated tubular member so as to facilitate placing said elongated tubular member over a flaccid penis;
   said elongated tubular member having an open base end and a closed, continuous, substantially smooth head end portion at the end thereof opposite said open end, said closed head end portion being adapted to cover a head portion of a penis and to contain ejaculated spermatozoa;
   said elongated opening having opposed edges and extending from said open base and along the length of said elongated tubular member, except for said closed head end portion of said elongated tubular member; and
   means for closing said elongated opening after placing of said condom on a flaccid penis, said closing means comprising a first elongated member on one of said edges of said elongated opening and defining an elongated groove-like receptacle which is substantially coextensive with said elongated opening, and a second elongated member extending along the other of said edges of said elongated opening and having an elongated projection thereon which is substantially coextensive with said elongated groove-like receptacle and which is lockingly and sealingly engageable in said groove-like receptacle to close said elongated opening along the complete length of the condom portion which extends along the penis after said condom is placed over a penis to provide a liquid tight closing of said elongated opening, said closing means presenting substantially smooth inner and outer surfaces along its length when in its liquid tight closed position.

2. The condom of claim 1, wherein said elongated tubular member includes protective means extending over said closing means.

3. The condom of claim 2, wherein said protective means comprises an elongated sleeve arranged over said elongated tubular member at least over the length of said condom along which said closing means extends.

4. The condom of claim 2, wherein said protective means comprises a roll-down sleeve which extends around the complete periphery of said elongated tubular member and which is initially rolled up so as to be rollable down along the length of said condom to extend the sleeve over the length of said closing means.

5. The condom of claim 1, wherein said protective means comprises a flap member extending from one end of said elongated opening, over said closing means, to the other end of said elongated opening.

6. The condom of claim 5, wherein said flap means integrally extends from said closed head end of said elongated tubular member.

7. The condom of claim 5, wherein said flap member extends externally of said elongated tubular member.

8. The condom of claim 5, wherein said flap member extends interior of said elongated tubular member.

9. The condom of claim 8, wherein said protective means further comprises a flap member extending externally of said elongated tubular member from one end of said elongated opening, over said closing means, to the other end of said elongated opening.

10. The condom of claim 1, wherein said closing means comprises a a slide which is slideable therealong to close said closing means.

11. The condom of claim 10, wherein said slide is removeable from the ends of said closing means after said slide is slid along said closing means to close said closing means.

12. The condom of claim 10, wherein said condom comprises stop means to prevent said slide from sliding off said closing means after closure of same, and wherein said elongated tubular member comprises protective means at the base end of said condom for covering said slide after said slide is slid along the length of said condom to close said closing means.

13. The condom of claim 12, wherein said protective means at said base end of said condom comprises sleeve means encircling the base end of said condom.

14. The condom of claim 13, wherein said sleeve means comprises roll-up sleeve means which is unrolled to form a sleeve.

* * * * *